United States Patent

Wettstein

[11] Patent Number: 5,942,678
[45] Date of Patent: Aug. 24, 1999

[54] METHOD FOR TRACING LEAKS IN THE CLOSED OR HALF-OPEN COOLING SYSTEM OF A GAS TURBINE

[75] Inventor: Hans Wettstein, Fislisbach, Switzerland

[73] Assignee: Asea Brown Boveri AG, Baden, Switzerland

[21] Appl. No.: 08/938,455

[22] Filed: Sep. 29, 1997

[30] Foreign Application Priority Data

Dec. 9, 1996 [DE] Germany .................. 196 51 073

[51] Int. Cl.$^6$ .................................................. G01M 3/20
[52] U.S. Cl. ................................... 73/40.7; 165/11.1
[58] Field of Search .............................. 73/40, 40.5 R, 73/40.7; 165/11.1, 11.2

[56] References Cited

U.S. PATENT DOCUMENTS

| 4,373,379 | 2/1983 | Obara et al. | 73/40.7 |
|---|---|---|---|
| 4,574,619 | 3/1986 | Castellant et al. | |
| 4,918,975 | 4/1990 | Voss | 73/40.7 |
| 5,070,723 | 12/1991 | Tsou et al. | 73/40.7 |
| 5,492,004 | 2/1996 | Berg et al. | 73/40.7 |

FOREIGN PATENT DOCUMENTS 0285864  10/1988  European Pat. Off. .
4033473A1  4/1992  Germany .

OTHER PUBLICATIONS

"Kuhleinrichtungen fur wasserstoff– und eassergekuhlte Turbogeneratoren", ABB Technik Aug. 1991, pp. 21–28.
Krafttfahr Technisches Taschenbuch, Robert Bosch GmbH, 1995, pp. 490–500.
Thermische Turbomaschinen, Traupel, 1988, p. 84.

*Primary Examiner*—Michael Brock
*Attorney, Agent, or Firm*—Burns, Doane, Swecker & Mathis, L.L.P.

[57] ABSTRACT

In the case of a method for tracing leaks in the closed or half-cooling system of a gas turbine installation, the parts of the gas turbine installation to be cooled being cooled by means of a cooling fluid (15) other than air, and the cooling fluid (15) flowing in a special cooling fluid circuit (16), and the leak in the cooling system leading to the cooling fluid (15), entering the hot gas channel of the gas turbine (3), samples are taken from the exhaust gas (10) from the gas turbine and concentration measurements, preferably of the cooling fluid (15), are carried out on these samples. The sample taking and concentration measurement may be carried out continuously or periodically. The concentration measurement results are passed to an alarm or a protection system (21) by means of which overheating of inadequately cooled parts of the turbine (3) is prevented.

22 Claims, 3 Drawing Sheets

METHOD FOR TRACING LEAKS IN THE CLOSED OR HALF-OPEN COOLING SYSTEM OF A GAS TURBINE

BACKGROUND OF THE INVENTION

1. Field of the Invention

The invention relates to the field of power station engineering. It concerns a method for tracing leaks in the closed or half-open cooling system of a gas turbine in which a coolant other than air flows in a special circuit.

2. Discussion of Background

In addition to air cooling, the idea of external cooling has also been pursued from the start in the design of gas turbines. In this type of cooling, the parts of the turbine are cooled by an external medium, generally water or water vapor, this coolant flowing in a special circuit (W. Traupel: Thermische Turbomaschinen, [Turbomachines], Springer Verlag, 1988, 3rd edition, Volume 1, 85). This coolant circuit may, for example, be closed, the minor leakages which can virtually never be avoided being compensated for by replenishment of coolant in the circuit. The coolant circuit may, for example, also be half-open, in that coolant is also deliberately extracted from the coolant circuit and is used, for example, for direct film cooling of thermally particularly severely loaded parts.

Particularly in the case of gas turbines having closed cooling systems, the development of a leak through which coolant flows out of the cooling system into the hot gas channel is a major risk. As a result of the escaping cooling fluid, there is no cooling fluid in the downstream cooling zones, resulting in rapid overheating of the affected parts.

SUMMARY OF THE INVENTION

Accordingly, one object of the invention is to avoid this disadvantage by developing a simple method for tracing leaks in the closed or half-open cooling system of gas turbines, which method allows monitoring to protect the machine.

According to the invention, this is achieved in that, in the case of a method according to the descriptive part of claim 1, samples are taken from the exhaust gas from the gas turbine, and concentration measurements are carried out on these samples. The sample taking and measurements may be carried out continuously (on-line) or periodically.

The advantages of the invention are that, with this method, leaks in the cooling system of the gas turbine can easily be found and overheating of endangered parts can thus be avoided by taking action in good time. The concentration measurement results can in this case be used for alarms or for automatic protection action, for example reducing the fuel flow rate or increasing the cooling vapor flow rate.

It is particularly expedient if the cooling fluid concentration, preferably water vapor concentration, in the exhaust gas is measured. Alternatively, the $CO_2$ or NOx concentration can optionally be measured.

Furthermore, it is advantageous if a tracer substance, preferably noble gases, deuterium or ammonia, is added to the cooling fluid circuit and the tracer substance concentration in the exhaust gas is measured, since the tracer substance can easily be detected. Particularly in the case of expensive tracer substances, their addition can also be carried out cyclically or periodically, with corresponding monitoring.

Finally, the concentration samples are advantageously taken in the region between the turbine outlet and the chimney or between the turbine outlet and the waste-heat boiler. As far as possible, a concentration sample is preferably taken downstream from the gas turbine but still upstream of the boiler, in order that leakages from the waste-heat boiler are not also detected in the measurement, and the measurement result is not corrupted.

If a plurality of tap-off points for the concentration samples are arranged in a plane which is located at right angles to the flow direction, it is also possible to detect the position of leaks.

Furthermore, it is expedient if the concentration samples are taken downstream from the waste-heat boiler or directly in the chimney. Because mixing has already taken place there, it is sufficient for a sample to be taken at only a single point, so that the effort for tracing leaks in the cooling system here is very low.

Finally, it is expedient if, in the case of a machine with sequential combustion, which essentially comprises, arranged successively in the flow direction, a compressor, a first combustion chamber, a high-pressure turbine, a second combustion chamber and a second turbine, and in which the high-pressure turbine is cooled by means of a closed cooling fluid circuit, for concentration samples to be taken between the high-pressure turbine and the second combustion chamber, the tap-off points being arranged distributed on the circumference.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Only those elements which are required for direct understanding of the invention are illustrated. The flow direction of the media is indicated by arrows.

DESCRIPTION OF THE PREFERRED EMBODIMENTS

Figure 1:
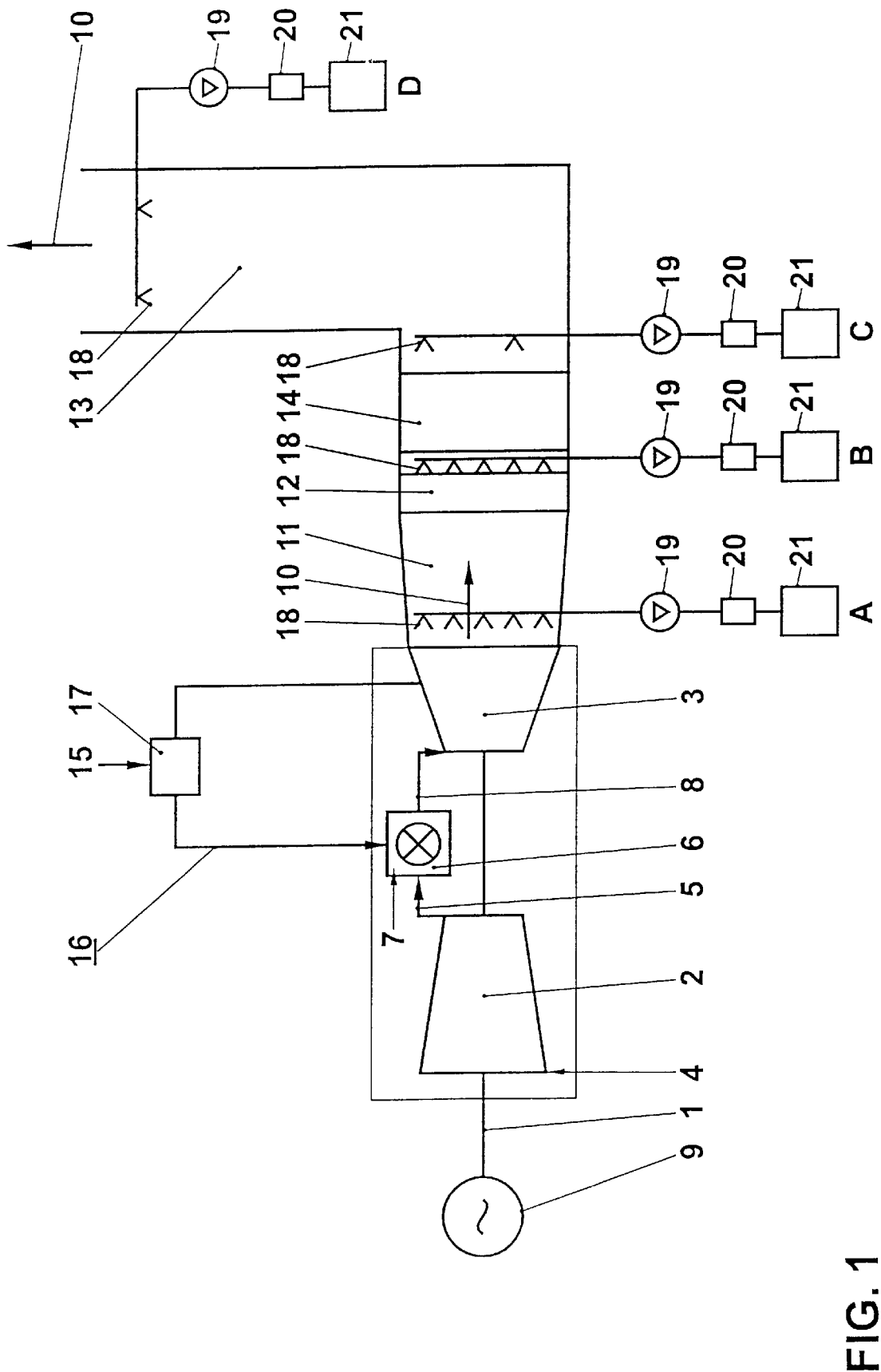
FIG. 1 shows a schematic illustration of a gas turbine installation with a closed cooling fluid circuit and with four different tap-off points for the concentration samples.
Figure 2:
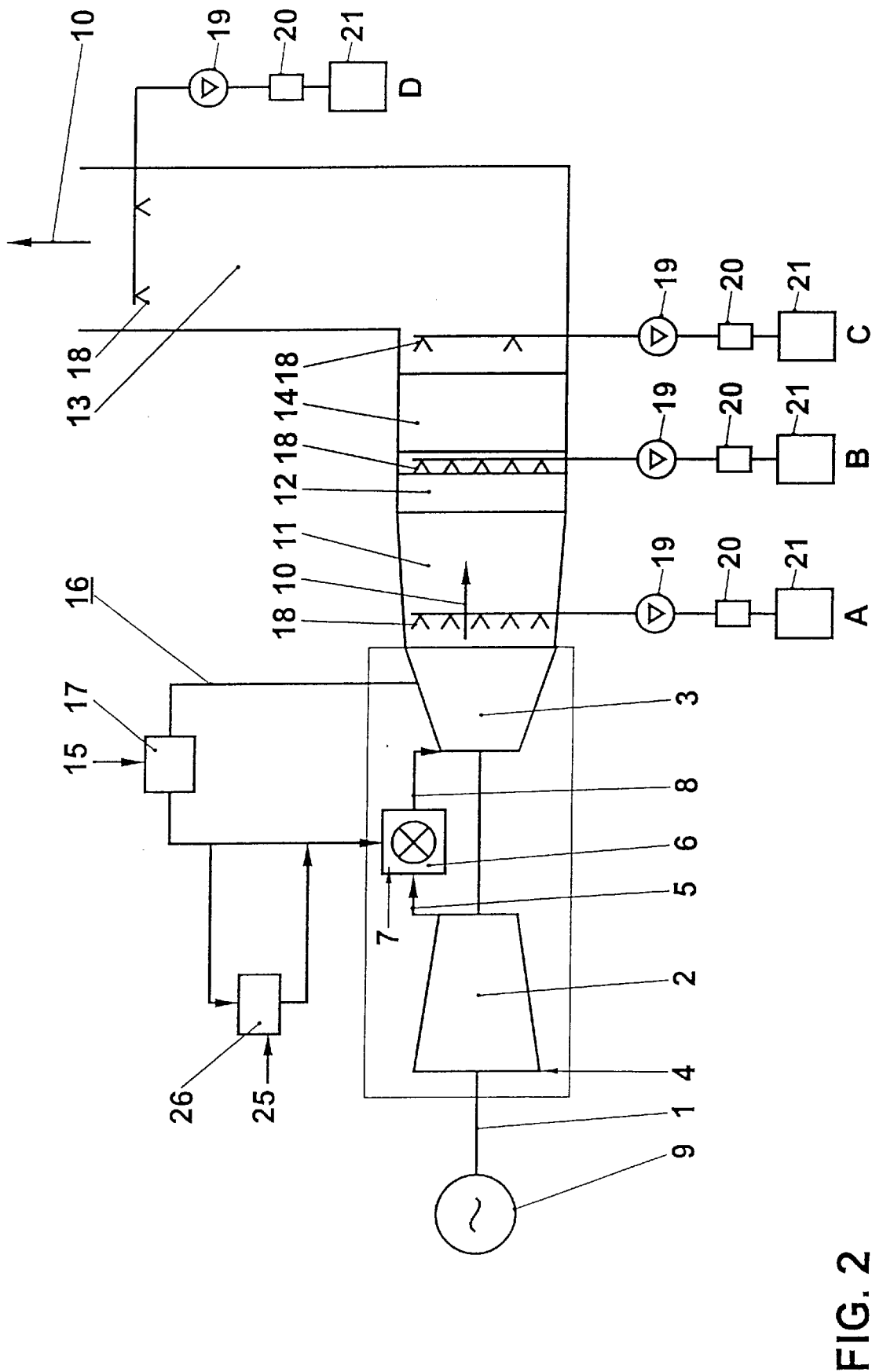
FIG. 2 shows a schematic illustration of a gas turbine installation analogous to FIG. 1, with additional tracer substance addition and control.
Figure 3:
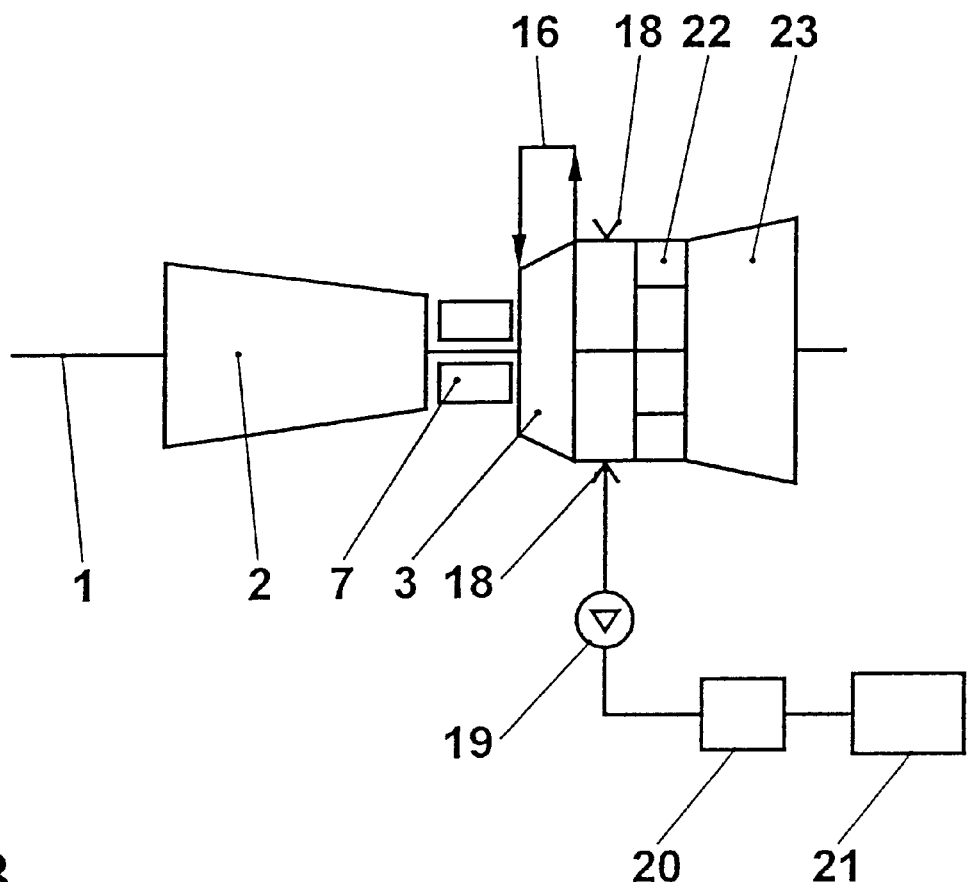
FIG. 3 shows a schematic illustration of a gas turbine installation with sequential combustion and concentration measurement according to the invention.

Referring now to the drawings, wherein like reference numerals designate identical or corresponding parts throughout the several views, an exemplary embodiment of the invention is explained in more detail in FIGS. 1 to 3.

FIG. 1 shows a schematic illustration of a gas turbine installation. A compressor 2 and a turbine 3 are arranged on a common shaft 1. Ambient air 4 is induced and is compressed in the compressor 2. This compressed air 5 is subsequently mixed with fuel 7 in a combustion chamber 6, and is burned. The hot gases 8 from the combustion chamber 6 then act on the turbine 3, where they expand. At the same time, the turbine 3 drives the compressor 2, which is connected to a generator 9 for electricity generation. The exhaust gases 10 from the turbine 3 then pass via an exhaust gas diffuser 11, a muffler 12 and a chimney 13 into the open air. It is possible to arrange upstream of the chimney a waste-heat boiler 14 in which heat is exchanged between the exhaust gas 10 and water or water vapor to be heated, and the exhaust gases 10 are cooled further. The gas turbine has a closed cooling system, parts of the turbine 3 and of the combustion chamber 7 being cooled by an external cooling fluid 15, generally water or water vapor, the cooling fluid 15 flowing in a special cooling fluid circuit 16. The cooling fluid circuit 16 is regulated by a cooling fluid flow rate control device 17, which is not described in any more detail here. Since it is impossible to avoid minor leakages occurring in practice, the cooling fluid circuit 16 must be regularly replenished with cooling fluid 15. To this extent, this is known prior art.

In the case of gas turbines with such a closed external cooling system, the development of leaks from the cooling system into the hot gas channel represents a major risk since the escape of cooling fluid 15 from the cooling fluid circuit 16 means that only a reduced cooling effect is now achieved in the downstream cooling zones, thus causing overheating of the affected turbine parts. For this reason according to the invention samples are taken from the exhaust gas 10 and concentration measurements are carried out on these samples. The sample taking and measurement in the case of this exemplary embodiment are carried out on-line. The cooling fluid concentration is preferably measured, that is to say if water vapor is used as the coolant 15, the water vapor concentration. Alternatively, it is possible to measure the $CO_2$ or $NO_x$ concentration.

As designated by the variants A, B, C and D of FIG. 1, the concentration samples can be taken from the exhaust gas flow at different points. The tap-off points 18 are in this case arranged in the region between the outlet from the turbine 3 and the chimney 13. In the case of variants A and B, the tap-off points 18 are arranged in the region between the outlet from the turbine 3 and the inlet to the waste-heat boiler 14. In this case, it is advantageous if the samples are taken from the exhaust gas flow as far as possible downstream from the turbine 3, but still upstream of the waste-heat boiler 14, in order that leakages from the waste-heat boiler 14 are not also detected.

If a plurality of tap-off points 18 are provided in a plane arranged at right angles to the flow direction of the exhaust gas 10, and concentration samples are taken there, it is possible by comparison of the measurements to determine the physical position of the leak.

In the case of variant C, the tap-off points 18 are provided directly downstream from the waste-heat boiler 14, and in variant D they are arranged in the chimney 13. The advantage of taking the samples at these points is that, because the exhaust gas 10 and the cooling fluid 15 have already been intensively mixed there, only a single tap-off point 18 is required. However, the measurements could be corrupted by any leaks in the boiler 14.

A common feature of all the variants A to D is that the exhaust gas samples are passed via pumps 19 to concentration test sets 20 in which the respective desired concentration is determined on-line. Subsequently, signals which correspond to the measurement results are passed to an alarm or protection system 21 which, for example, initiates a reduction in the fuel flow rate or an increase in the cooling vapor. These systems 21 act whenever, for example, an upper limit of the cooling fluid concentration is exceeded, the limit being predetermined as a function of one or more of the following operating parameters: power, inlet guide vane position, that is to say airflow rate, fuel type, amounts of water or vapor injected into the combustion chamber. The alarm or protection system 21 can also be active if, for example, an upper limit of the concentration ratio of cooling fluid ($H_2O$) to $CO_2$ is exceeded. It is advantageous here that the influence of power and airflow rate are largely neutralized.

If, in contrast, a lower limit which is likewise predetermined by the abovementioned operating parameters is undershot, then this can be used to detect faults in the measurement system.

In another exemplary embodiment analagous to FIG. 1, the sample taking from the exhaust gas 10 and the concentration measurement can also be carried out cyclically or periodically.

FIG. 2 shows a further design variant of the invention. FIG. 2 differs from the first design variant described above only in that a tracer substance 25 is added to the cooling fluid 15 in the cooling fluid circuit 16. Noble gases, deuterium or ammonia are particularly suitable for use as tracer substances 25. A tracer substance concentration flow rate control device 26 allows the measured concentration values of the tracer substance 25 to be compared with predetermined values and to be matched to the respective conditions by appropriate metering of the tracer substance 25. According to the invention, the concentration of the tracer substance 25 in the exhaust gas can advantageously be measured in such a case, it being possible to arrange the tap-off points 18 in the same way as described in conjunction with FIG. 1. The concentration test sets 20 are thus used to measure the tracer substance concentration, to compare this concentration with predetermined tracer substance limits and, if necessary, to switch on the alarm or protection system 21. The addition and concentration measurements of the tracer substance 25 can be carried out both continuously and, in a further exemplary embodiment, cyclically or periodically. Thus, for example, a specific amount of tracer substance 25 can be fed into the cooling fluid 15, and the concentration of the tracer substance 25 in the exhaust gas 10 can be measured as a function of time. The cooling system is then sealed to a greater extent the higher and narrower the "concentration peak" is (as a function of time). Such checks can be carried out periodically during operation of the gas turbine, for example once a day. Automatic initiation of these check measurements is possible. By taking samples from the exhaust gas and measuring the concentrations at shorter intervals only if the measurement results are poor, it is possible to save cost and tracer substance quantities.

The method according to the invention is most suitable for detection of leaks in closed cooling systems of a gas turbine, but can also be used for half-open cooling systems. Depending on the tracer content, injections can exacerbate detection.

FIG. 3 shows a further exemplary embodiment of the invention based on a gas turbine with sequential combustion. This essentially comprises, arranged on a common shaft 1, a compressor 2, a first high-pressure turbine 3 and a second turbine 23. Arranged between the compressor 2 on the first turbine 3 there is a first combustion chamber 7 in which the compressed air from the compressor 2 is mixed with fuel 6 and is burned. The hot gas produced is fed to the first high-pressure turbine 3, expands there, and the exhaust gas is fed to a second combustion chamber, the afterburner chamber 22, which is arranged between the first turbine 3 and the second turbine 23, and which provides the hot gas for application to the second turbine 23. As is indicated schematically in FIG. 3, parts of the high-pressure turbine 3 are cooled by means of a closed cooling fluid circuit 16. Water vapor can be used, for example, as the cooling fluid 15, to which, as already described above, a tracer substance 25 can additionally be added.

According to the invention, the high-pressure turbine 3 can now be monitored separately by taking concentration samples from the gas flow, from tap-off points 18 arranged on the circumference, in the region between the outlet from the high-pressure turbine 3 and the inlet to the afterburner chamber 22. The gas is conveyed by means of a pump 19 into the concentration test set 20, the measured values are compared with predetermined values and, if required, the alarm or protection system 21 is switched on. As already described above, it is possible to use not only cooling fluid concentration measured values, but also measured values of the concentrations of NOx, carbon dioxide or, possibly of a tracer substance.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for tracing leaks in the closed or half-open cooling system of a gas turbine installation, the parts of the gas turbine installation to be cooled being cooled by means of a cooling fluid (15) other than air, and the cooling fluid (15) flowing in a special cooling fluid circuit (16), and the leak in the cooling system leading to the cooling fluid (15) entering the hot gas channel of the gas turbine (3), wherein samples are taken from the exhaust gas (10) from the gas turbine (3) and concentration measurements are carried out on these samples.

2. The method as claimed in claim 1, wherein the sample taking and the concentration measurement are carried out on-line.

3. The method as claimed in claim 1, wherein the sample taking and the concentration measurement are carried out periodically.

4. The method as claimed in claim 1, wherein the cooling fluid concentration is measured.

5. The method as claimed in claim 4, wherein water vapor is used as the cooling fluid (15), and the water vapor concentration is measured.

6. The method as claimed in claim 1, wherein the $CO_2$ concentration is measured.

7. The method as claimed in claim 1, wherein the NOx concentration is measured.

8. The method as claimed in claim 1, wherein a tracer substance (25) is added to the cooling fluid circuit (16), and the tracer substance concentration in the exhaust gas (10) is measured.

9. The method as claimed in claim 8, wherein noble gases are used as the tracer substance (25).

10. The method as claimed in claim 8, wherein ammonia is used as the tracer substance (25).

11. The method as claimed in claim 8, wherein deuterium is used as the tracer substance (25).

12. The method as claimed in claim 8, wherein the addition of the tracer substance (25) into the cooling fluid circuit is carried out periodically.

13. The method as claimed in claim 1, wherein the samples are taken in a region between an outlet from the turbine (3) and a chimney (13).

14. The method as claimed in claim 13, wherein the samples are taken at a plurality of tap-off points (18) located in a plane at right angles to the flow direction.

15. The method as claimed in claim 1, wherein the samples are taken in a region between an outlet from the turbine (3) and an inlet to a waste heat boiler (14).

16. The method as claimed in claim 15, wherein the samples are taken as far as possible downstream from the gas turbine (3) but still upstream of the waste-heat boiler (13).

17. The method as claimed in claim 1, wherein the samples are taken immediately after an outlet from a waste-heat boiler (13).

18. The method as claimed in claim 17, wherein the samples are taken at only a single point.

19. The method as claimed in claim 1, wherein the samples are taken in a chimney (14).

20. The method as claimed in claim 1, the gas turbine installation being a machine with sequential combustion, which essentially comprises, arranged successively in the flow direction, a compressor (2), a first combustion chamber (7), a high-pressure turbine (3), a second combustion chamber (22) and a second turbine (23), a hot-gas channel (24) being provided between the high-pressure turbine (3) and the second combustion chamber (22), and in which the high-pressure turbine (3) is cooled by means of a closed or half-open cooling fluid circuit (16), wherein concentration samples are taken from the gas flow between the high-pressure turbine (3) and the second combustion chamber (22), tap-off points (18) being arranged distributed on the circumference of the hot-gas channel (24).

21. The method as claimed in claim 1, wherein the concentration measurement results are passed to an alarm system (21).

22. The method as claimed in claim 1, wherein the concentration measurement results are passed to an automatic protection system.

* * * * *